United States Patent
Richards

(10) Patent No.: US 11,039,992 B2
(45) Date of Patent: *Jun. 22, 2021

(54) STABLE REDOX COMPOSITIONS AND METHODS OF USE

(71) Applicant: Reoxcyn, LLC, Pleasant Grove, UT (US)

(72) Inventor: Kurt Richards, Herriman, UT (US)

(73) Assignee: REOXYCN, LLC, South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/381,915

(22) Filed: Apr. 11, 2019

(65) Prior Publication Data

US 2019/0328632 A1 Oct. 31, 2019

Related U.S. Application Data

(63) Continuation of application No. 16/125,344, filed on Sep. 7, 2018, now Pat. No. 10,292,911.

(60) Provisional application No. 62/609,714, filed on Dec. 22, 2017.

(51) Int. Cl.

| | | |
|---|---|---|
| *A61K 8/19* | (2006.01) |
| *A61K 47/02* | (2006.01) |
| *A61Q 19/00* | (2006.01) |
| *A61K 47/34* | (2017.01) |
| *A61K 8/891* | (2006.01) |
| *A61K 8/20* | (2006.01) |
| *A61Q 19/08* | (2006.01) |
| *A61K 8/04* | (2006.01) |
| *A61K 9/06* | (2006.01) |
| *A61K 9/00* | (2006.01) |
| *A61K 8/24* | (2006.01) |
| *A61K 8/26* | (2006.01) |
| *A61K 8/96* | (2006.01) |

(52) U.S. Cl.
CPC ............ *A61K 8/19* (2013.01); *A61K 8/042* (2013.01); *A61K 8/20* (2013.01); *A61K 8/24* (2013.01); *A61K 8/26* (2013.01); *A61K 8/891* (2013.01); *A61K 8/965* (2013.01); *A61K 9/0014* (2013.01); *A61K 9/0053* (2013.01); *A61K 9/0095* (2013.01); *A61K 9/06* (2013.01); *A61K 47/02* (2013.01); *A61K 47/34* (2013.01); *A61Q 19/00* (2013.01); *A61Q 19/08* (2013.01); *A61K 2800/83* (2013.01)

(58) Field of Classification Search
CPC .... A61K 2800/83; A61K 47/02; A61K 47/34; A61K 8/042; A61K 8/19; A61K 8/20; A61K 8/24; A61K 8/26; A61K 8/891; A61K 8/965; A61K 9/0014; A61K 9/0053; A61K 9/0095; A61K 9/06; A61Q 19/00; A61Q 19/08
See application file for complete search history.

(56) References Cited

U.S. PATENT DOCUMENTS

| | | | |
|---|---|---|---|
| 9,833,471 B1 | 12/2017 | Richards et al. | |
| 10,292,911 B1 * | 5/2019 | Richards | A61Q 19/00 |
| 10,485,827 B2 * | 11/2019 | Hoover | A61K 47/02 |
| 10,828,325 B2 * | 11/2020 | Richards | A61K 33/20 |
| 2009/0162443 A1 * | 6/2009 | Anthony | A61K 8/31 424/489 |
| 2009/0214628 A1 | 8/2009 | de Rijk | |
| 2011/0076244 A1 | 3/2011 | Hammer | |
| 2013/0344202 A1 * | 12/2013 | Addison | A23L 27/40 426/73 |
| 2016/0317577 A1 * | 11/2016 | Hoover | A61K 47/32 |
| 2017/0202877 A1 | 7/2017 | Hoover et al. | |

OTHER PUBLICATIONS

Downie, JB. (Practical Dermatology for Pediatrics. 2010; pp. 19-22) (Year: 2010).*
Minerals in Himalayan Pink Salt: Spectral Analysis [online] retrieved on Nov. 16, 2020 from: https://themeadow.com/pages/minerals-in-himalayan-pink-salt-spectral-analysis; 6 pages. (Year: 2020).*
Pass the salt [online] retrieved on Nov. 5, 2018 from: https://sciencebasedmedicine.org/pass-the-salt-but-not-that-pink-himalayan-stuff/; Aug. 19, 2014; 17 pages (Year: 2014).
International Search Report and Written Opinion issued in application No. PCT/US2018/066902, dated Apr. 8, 2019.

* cited by examiner

*Primary Examiner* — Ernst V Arnold
(74) *Attorney, Agent, or Firm* — Knobbe, Martens, Olson & Bear LLP

(57) ABSTRACT

Described herein are compositions that include a saline solution and reactive oxygen species. Specifically, the composition may include a saline solution, reactive oxygen species, an emollient, and a pH modifier. Also provided is a gel composition that includes a rheology agent. Also provided are methods of making and using the compositions.

17 Claims, No Drawings

STABLE REDOX COMPOSITIONS AND METHODS OF USE

RELATED APPLICATIONS

This application is a continuation application of U.S. patent application Ser. No. 16/125,344, filed on Sep. 7, 2018, which claims the benefit of priority to U.S. Provisional Patent Application No. 62/609,714, filed Dec. 22, 2017, the disclosure of which is incorporated by reference herein in its entirety.

FIELD

The present disclosure relates to stable redox compositions that include a saline solution, a reactive oxygen species, an emollient, and a pH modifying agent, wherein the saline solution includes a salt. Also provided are compositions that further include a rheology agent. The disclosure also relates to methods of making and using the compositions.

BACKGROUND

Salinated compositions having reactive oxygen species are frequently used for cosmetic, personal, medicinal, or industrial uses. A wide variety of formulations are known, and may include, for example, formulations for topical application for improving the appearance of skin, for preventing skin aging, for moisturizing, for wound healing, or for general applications.

Reactive oxygen species (ROS) are important in a variety of fields. In medicine there is evidence linking ROS to the aging, disease processes, and the reduction of oxidative stress. Furthermore, ROS are employed as microbicidal agents in the home, hospital, and other settings.

There is a need in the art for improved formulations that include reactive oxygen species, such that the formulation is stable, effective, and has desirable characteristics.

SUMMARY

The present disclosure is directed to compositions having reactive oxygen species and methods of making and using the same.

In some embodiments, the composition includes a saline solution, a reactive oxygen species, an emollient, and a pH modifying agent. In some embodiments, the composition further includes a rheology agent. In some embodiments, the saline solution includes salt in an amount of about 0.001% to about 15% w/v, such as 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5%, 6%, 7%, 8%, 9%, 10%, 11%, 12%, 13%, 14%, or 15% w/v or an amount within a range defined by any two of the aforementioned values. In some embodiments, the salt is purified or refined salt, such as table salt. In some embodiments, the salt is raw, unprocessed salt. In some embodiments, the salt is Himalayan sea salt.

In some embodiments, the reactive oxygen species includes superoxides ($O_2^{*-}$, $HO_{2*}$), hypochlorites ($OCl^-$, $HOCl$, $NaClO$), hypochlorates ($HClO_2$, $ClO_2$, $HClO_3$, $HClO_4$), oxygen derivatives ($O_2$, $O_3$, $O_4^*$, $O$), hydrogen derivatives ($H_2$, $H^-$), hydrogen peroxide ($H_2O_2$), hydroxyl free radical ($OH^{*-}$), ionic compounds ($Na^+$, $Cl^-$, $H^+$, $OH^-$, $NaCl$, $HCl$, $NaOH$), chlorine ($Cl_2$), water clusters ($n*H_2O$—induced dipolar layers around ions), and combinations thereof. In some embodiments, the reactive oxygen species is hypochlorite. In some embodiments, the reactive oxygen species is present in an amount of about 5 to about 100 ppm, such as 5, 10, 15, 20, 25, 30, 35, 40, 45, 50, 55, 60, 65, 70, 75, 80, 85, 90, 95, or 100 ppm, or an amount within a range defined by any two of the aforementioned values.

In some embodiments, the emollient is a silicone polymer or blend thereof, such as dimethicone, cyclomethicone, or a blend thereof. In some embodiments, the emollient is present in an amount of about 0.5% to about 10% w/v, such as 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10.0% w/v, or an amount within a range defined by any two of the aforementioned values. In some embodiments, the pH modifying agent is a buffer, a base, or an acid, such as sodium phosphate monobasic. In some embodiments, the pH modifying agent is present in an amount of about 0.05% to about 5% w/v, such as 0.05%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, or 5.0% w/v, or an amount within a range defined by any two of the aforementioned values.

In some embodiments, the rheology agent is sodium magnesium silicate. In some embodiments, the rheology agent is present in an amount of about 0.5% to about 10% w/v, such as 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10.0% w/v, or an amount within a range defined by any two of the aforementioned values.

In some embodiments, the composition includes a saline solution having salt in an amount of about 0.05% w/v, hypochlorite in an amount of about 72 ppm, sodium magnesium silicate in an amount of about 3.25% w/v, a silicone polymer in an amount of about 5% w/v, and sodium phosphate monobasic in an amount of about 0.3% w/v.

In some embodiments, the composition is formulated as a gel, sol, sol-gel, hydrogel, cream, foam, balm, liniment, unguent, colloid, emulsion, dispersion, salve, emollient, lotion, meltable solid, mousse, ointment, paste, serum, solution, a liquid, spray, stick, or suspension.

Some embodiments relate to methods of making one or more of the composition disclosed herein. In some embodiments, the method includes providing a saline solution having reactive oxygen species therein, and mixing an emollient with the saline solution. In some embodiments, the saline solution having reactive oxygen species could be made by electrolyzing a saline solution. In some embodiments, the method further includes making a gel composition by further providing a rheology agent and mixing the rheology agent with the saline solution.

Some embodiments provided herein relate to methods of using the composition as described herein. In some embodiments, the method includes administering or applying an amount of a composition to a subject in need thereof. In some embodiments, the composition is formulated for ingestion, for injection, or for topical application. Some embodiments provided herein relate to methods of using a composition. In some embodiments, the methods include administering the composition as described herein to a subject. In some embodiments, the methods include providing the composition as described herein in a topical formulation to a subject.

DETAILED DESCRIPTION

Embodiments provided herein related to a reactive oxygen salinated composition. In some embodiments, the composition includes a saline solution, a reactive oxygen species, an emollient, and a pH modifier. In some embodiments, the composition further includes a rheology agent. Also provided are methods of making and methods of using the composition.

It will be readily understood that the aspects of the present disclosure, as generally described herein, can be arranged, substituted, combined, separated, and designed in a wide variety of different configurations, all of which are explicitly contemplated herein.

Unless defined otherwise, technical and scientific terms used herein have the same meaning as commonly understood by one of ordinary skill in the art to which the present disclosure belongs. All patents, applications, published applications and other publications referenced herein are expressly incorporated by reference in their entireties unless stated otherwise. For purposes of the present disclosure, the following terms are defined below.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. When a value is preceded by the term about, the component is not intended to be limited strictly to that value, but it is intended to include amounts that vary from the value.

Throughout this specification, unless the context requires otherwise, the words "comprise," "comprises," and "comprising" will be understood to imply the inclusion of a stated step or element or group of steps or elements but not the exclusion of any other step or element or group of steps or elements.

I. Redox Compositions

Some embodiments provided herein relate to a reactive oxygen salinated composition. As used herein, the term "composition" or "formulation" as used herein refers to a combination of elements, components, or compositions presented together for a given purpose.

In some embodiments, the "purity" of any given agent (for example, hypochlorous acid or a buffer) in a composition may be specifically defined. For instance, certain compositions may include, for example, an agent that is at least 80, 85, 90, 91, 92, 93, 94, 95, 96, 97, 98, 99, or 100% pure, including all decimals in between, as measured, for example and by no means limiting, by analytical chemistry techniques.

As used herein, the term "saline solution" refers to a solution having a quantity of salt. In some embodiments, the saline solution includes a purified or refined salt. In some embodiments, the saline solution includes a raw or unprocessed salt. In some embodiments, the salt is halite, table salt, refined salt, curing salt, flake salt, Epsom salt, sea salt, Alaea salt (or Hawaiian sea salt), Alpenbergkern salt, Anglesey Sea salt, Celtic sea salt, Dead Sea salt, Himalayan sea salt (including Himalayan pink sea salt), Kalahari salt, Maras salt, Murray River salt flakes, Namibian salt pearls, Persian blue fine salt, Polish mine salt, primordial sea salts, Sal de Tavira, Sale Marino di Trapani, Sel de Guérande, South African Sea salt, Utah salt, black lava salt, brine, rock salt, red rock salt, fleur de sel, or kosher salt. The salt present in the saline solution can include a number of elements, including actinium, aluminum, antimony, arsenic, astatine, barium, beryllium, bismuth, boron, bromine, cadmium, calcium, carbon, cerium, cesium, chlorine, chromium, cobalt, copper, dysprosium, erbium, europium, francium, fluorine, gadolinium, gallium, germanium, gold, hafnium, holmium, hydrogen, iodine, indium, iridium, iron, lanthanum, lead, lithium, lutetium, magnesium, manganese, mercury, molybdenum, neptunium, neodymium, nickel, niobium, nitrogen, osmium, oxygen, palladium, phosphorus, platinum, plutonium, polonium, potassium, praseodymium, promethium, protactinium, radium, rhenium, rhodium, rubidium, ruthenium, samarium, scandium, selenium, silicon, silver, sodium, strontium, sulfur, tantalum, technetium, tellurium, terbium, thallium, thorium, thulium, tin, titanium, uranium, vanadium, ytterbium, zinc, or zirconium. In some embodiments, the element present in the salt can be present in an amount of less than 0.001 ppm to an amount of greater than 400,000 ppm. In some embodiments, the saline solution includes salt in an amount of 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5, 6, 7, 8, 9, 10, 11, 12, 13, 14, or 15% (w/v), or an amount within a ranged defined by any two of the aforementioned values. In some embodiments, the saline solution includes salt in an amount of 0.05%.

As used herein, the term "reactive oxygen species (ROS)" refers to chemically reactive molecules containing oxygen. Examples include ozone, peroxides, active chlorines, active oxygens, superoxides, active hydrogens, hydroxyl radical, and singlet oxygen. ROS are formed as a natural byproduct of the normal metabolism of oxygen and have important roles in cell signaling and homeostasis. ROS can include, but are not limited to superoxides ($O_2^{*-}$, $HO_{2*}$), hypochlorites ($OCl^-$, $HOCl$, $NaClO$), hypochlorates ($HClO_2$, $ClO_2$, $HClO_3$, $HClO_4$), oxygen derivatives ($O_2$, $O_3$, $O_4^{*-}$, $O$), hydrogen derivatives ($H_2$, $H$), hydrogen peroxide ($H_2O_2$), hydroxyl free radical ($OH^*$), ionic compounds ($Na^+$, $Cl^-$, $H^+$, $OH^-$, $NaCl$, $HCl$, $NaOH$), chlorine ($Cl_2$), water clusters ($n*H_2O$—induced dipolar layers around ions), and combinations thereof. Some ROS can be electron acceptors and some can be electron donors. In some embodiments, a reactive oxygen species is a hypochlorite. In one embodiment, the composition can include at least one reactive oxygen species such as $O_2$, $H_2$, $Cl_2$, $OCl^-$, $HOCl$, $NaOCl$, $HClO_2$, $ClO_2$, $HClO_3$, $HClO_4$, $H_2O_2$, $Na^+$, $Cl^-$, $H^+$, $OH^-$, $O_3$, $O_4^{*-}$, $^1O$, $OH^{*-}$, $HOCl$—$O_2^{*-}$, $HOCl$—$O_3$, $O_2^{*-}$, $HO_2^*$, $NaCl$, $HCl$, $NaOH$, water clusters, or a combination thereof.

Redox signaling deals with the action of a set of several simple reactive signaling molecules that are mostly produced by mitochondria residing inside cells during the metabolism of sugars. These reactive signaling molecules are categorized into two general groups, ROS, which contain oxidants, and reduced species (RS), which contain reductants. These fundamental universal signaling molecules in the body are the simple but extremely important reactive signaling molecules that are formed from combinations of the atoms (Na, Cl, H, O, N) that are readily found in the saline bath that fills the inside of the cells (cytosol). All of the molecular mechanisms inside healthy cells float around in this saline bath and are surrounded by a balanced mixture of such reactive signaling molecules. A few examples of the more than 20 reactive molecules formed from these atoms inside the cell, some of which are discussed herein, are superoxide, hydrogen peroxide, hypochlorite, and nitric oxide.

Such reactive signaling molecules are chemically broken down by specialized enzymes placed at strategic locations inside the cell. Some of these protective enzymes are classified as antioxidants such as glutathione peroxidase and superoxide dismutase. In a healthy cell, the mixtures of these reactive signaling molecules are broken down by the antioxidant enzymes at the same rate that they are produced by the mitochondria. As long as this homeostatic balance is maintained, the cell's chemistry is in balance and all is well.

When damage occurs to the cell, for any number of reasons, including bacterial or viral invasion, DNA damage, physical damage or toxins, this homeostatic balance is disturbed and a build-up of oxidants or reductants occurs in the cell. This condition is known as oxidative stress and it acts as a clear signal to the cell that something is wrong. The cell reacts to this signal by producing the enzymes and repair molecules necessary to attempt repairs to the damage and it also can send messengers to activate the immune system to identify and eliminate threats. If oxidative stress persists in the cell for more than a few hours, then the cell's repair attempts are considered unsuccessful and the cell kills and dismantles itself and is replaced by the natural cellular division of healthy neighboring cells.

On a cellular level, this is essentially the healthy tissue maintenance process: damaged cells are detected and repaired or replaced by healthy cells. This cellular repair and regeneration process is constantly taking place, millions of times an hour, in all parts of the body.

In one embodiment, the composition can include at least one reactive oxygen species such as $H_2$, $Cl_2$, $OCl^-$, $HOCl$, $NaOCl$, $HClO_2$, $ClO_2$, $HClO_3$, $HClO_4$, $H_2O_2$, $O_3$, $O_4^{*-}$, $^1O_2$, $OH^{*-}$, $HOCl-_2^{*-}$, $HOCl-O_3$, $O_2^{*-}$, $HO_2^*$, water clusters, or a combination thereof.

In one embodiment, the composition can include at least one reactive oxygen species such as $HClO_3$, $HClO_4$, $H_2O_2$, $O_3$, $O_4^{*-}$, $^1O_2$, $OH^{*-}$, $HOCl-O_2^{*-}$, $HOCl-O_3$, $O_2^{*-}$, $HO_2^*$, water clusters, or a combination thereof. In one embodiment, the composition can include at least $O_2^*$— and HOCl.

In one embodiment, the composition can include $O_2$. In one embodiment, the composition can include Hz. In one embodiment, the composition can include $Cl_2$. In one embodiment, the composition can include $OCl^-$. In one embodiment, the composition can include HOCl. In one embodiment, the composition can include NaOCl. In one embodiment, the composition can include $HClO_2$. In one embodiment, the composition can include $ClO_2$. In one embodiment, the composition can include $HClO_3$. In one embodiment, the composition can include $HClO_4$. In one embodiment, the composition can include $H_2O_2$. In one embodiment, the composition can include $Na^+$. In one embodiment, the composition can include $Cl^-$. In one embodiment, the composition can include $H^+$. In one embodiment, the composition can include $H^-$. In one embodiment, the composition can include $OH^-$. In one embodiment, the composition can include $O_3$. In one embodiment, the composition can include $O_4^{*-}$. In one embodiment, the composition can include $^1O_2$. In one embodiment, the composition can include $OH^{*-}$. In one embodiment, the composition can include $HOCl-O_2^{*-}$. In one embodiment, the composition can include $HOCl-O_3$. In one embodiment, the composition can include $O_2^{*-}$. In one embodiment, the composition can include $HO_2^*$. In one embodiment, the composition can include NaCl. In one embodiment, the composition can include HCl. In one embodiment, the composition can include NaOH. In one embodiment, the composition can include water clusters. Embodiments can include combinations thereof.

"Hypochlorous acid", as used herein, refers to a weak acid having the chemical formula HClO. Hypochlorous acid is also known as chloric (I) acid, chloranol, or hydroxidochlorine. Hypochlorite includes ions of hypochlorous acid (for example, $OCl^-$). Salts of hypochlorite are also referred to herein and can include sodium hypochlorite (NaClO), calcium hypochlorite ($Ca(ClO)_2$), or potassium hypochlorite (KClO). Hypochlorite, or acids and salts thereof, may be present in the compositions described herein in an amount of 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 1%, 5%, 10%, 15%, 20%, 25%, 30%, 40%, 50%, or greater w/v %, or within a range defined by any two of the aforementioned amounts. In some embodiments, the w/v % of hypochlorite or an acid or salt thereof is 0.072% w/v. In some embodiments, the hypochlorite, or salt or acid thereof, is added directly to a composition. In some embodiments, the hypochlorite, or acid or salt thereof, is generated in the composition by electrolysis. In some embodiments, the final amount of hypochlorite is less than, greater than, or equal to about 10, 15, 20, 25, 30, 35, 40, 45, 50, 55, 60, 65, 70, 75, 80, 85, 90, 95, 100, 120, 150, 175, 200, 300 ppm or within a range defined by any two of the aforementioned amounts. In some embodiments, the amount of hypochlorite in the composition is between about 50 to about 100 ppm. In some embodiments, the amount of hypochlorite in the composition is about 72 ppm.

As used herein, an "emollient" refers to a compound that soothes the skin. In some embodiments, an emollient is a moisturizer, a cream, a lotion, an oil, a rub, a salve, an unguent, or a balm. In some embodiments, the emollient is a silicone polymer. In some embodiments, the silicone polymer is dimethicone, which is also referred to as polydimethylsiloxane (PDMS), dimethylpolysiloxane, E900, or polymerized siloxane and has the chemical formula of $CH_3[Si(CH_3)_2O]_nSi(CH_3)_3$ where n is the number of repeating monomer $[Si(CH_3)_2]$ units. Silicone polymers also include cyclomethicone, which is a cyclic siloxane. In some embodiments, the silicone polymer used in the composition is a blend of dimethicone and cyclomethicone. In some embodiments, the silicone polymer is dimethicone satin, a mixture of low and high molecular weight linear silicones. In some embodiments, the silicone polymer is amodimethicone, cyclo-dimethicone, cyclomethicone, dimethicone 500, dimethicone satin, iso-dimethicone copolymer, or blends thereof. In some embodiments, a silicone polymer acts as a moisturizer, a slip agent, or a lubricant. The emollient may be present in the composition in an amount of about 0.5%, 1%, 5%, 10%, 15%, 20%, 30%, 40%, 50%, or greater w/v %, or in an amount within any two of the aforementioned values or between a range defined by these values. In some embodiments, the amount of silicone polymer is about 5% w/v.

As used herein, the term "pH modifier" refers to an acid, base, or agent that may be used to change or stabilize the pH of a composition. A pH modifier may include an agent for modifying the pH of a solution or composition, such as an acid or a base, including, for example, mineral acids such as hydrochloric acid, phosphoric acid and sulfuric acid, organic acids such as benzoic acid, citric acid, lactic acid, maleic acid, malic acid, tartaric acid, adipic acid, gluconic acid and their salts and bases such as sodium hydroxide and potassium hydroxide. In some embodiments, a pH modifier may include an agent for stabilizing the pH of a solution or composition at a desired pH, including for example, a buffer such as a sodium acetate, acetate, citrate, or phosphate buffer. In some embodiments, the pH modifier is sodium phosphate monobasic. In some embodiments, the pH modifier is present in an amount of about 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or 15% w/v, or an amount within a range defined by any two of the aforementioned values. In some embodiments, the pH modifier is present in an amount of about 0.3% w/v. As used herein, the pH of the composition is the numerical scale to specify the acidity or basicity of the composition. In some embodiments, the pH of the composition is about 5.0 to about 8.5, such as 5.0, 5.5, 6.0, 6.5, 6.6, 6.7, 6.8, 6.9, 7.0, 7.1, 7.2, 7.3, 7.4, 7.5, 7.6, 7.7, 7.8, 7.9, 8.0, or 8.5, or within a ranged defined by any two of the aforementioned values. In some embodiments, the pH of the composition is in a range from about 6.0 to about 7.8.

In some embodiments, the composition described herein have osmolality measurement values of about 0.5 to 100 mOsm/kg, such as 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 80, 90, or 100 mOsm/kg, or within a range defined by any two of the aforementioned values. In some embodiments, the compositions have osmolality measurement vales of about 3 to 5 mOsm/kg.

In some embodiments, the composition further includes a rheology agent. As used herein, the term "rheology agent" refers to a substance that modulates the viscosity of a composition, without modifying other properties of the composition. In some embodiments, the rheology agent acts as a thickener by increasing the viscosity of the composition. In some embodiments, the rheology agent can include a metal silicate. In some embodiments, the rheology agent is sodium magnesium silicate, a silicate of sodium and magnesium. In some embodiments, sodium magnesium silicate is a synthetic silicate clay, having magnesium and sodium silicate. In some embodiments, a rheology agent is used as a binder and bulking agent in cosmetics and personal care products, in part because of its ability to absorb water. Sodium magnesium silicate is effective in slowing the decomposition of formulas, and can prevent premature darkening of compositions and prevent premature development of a foul odor, thereby improving the shelf life of cosmetic compositions. In some embodiments, the sodium magnesium silicate is Laponite, including for example, Laponite XL21™, Laponite RD™, Laponite RDS™, Laponite S482™, Laponite SL25™, Laponite EP™, Laponite JS™, Laponite XLS™, Laponite D™, or Laponite XLG™. The rheology agent may be used in the composition in an amount of about 0.1%, 0.25%, 0.5%, 0.75%, 1%, 1.5%, 2%, 2.5%, 3%, 3.5%, 4%, 4.5%, 5%, 6%, 7%, 10%, 15%, or greater w/v %, or in an amount within any two of the aforementioned values or between a range defined by these values. In some embodiments, the amount of rheology agent is about 3% w/v.

In some embodiments, the viscosity of the composition can be any suitable viscosity for the mode of administration. Thus, for oral administration, such as when the composition is formulated as a liquid for oral administration, the viscosity is similar to the viscosity of pure water. In some embodiments, the composition is a suitable viscosity such that the composition can be topically applied to a subject. In some embodiments, the viscosity of the composition can be in the range of about 1 to about 100,000 centipoise (cP). In some embodiments, the viscosity of the composition can be 1, 100 cP, 200 cP, 300 cP, 400 cP, 500 cP, 600 cP, 700 cP, 800 cP, 900 cP, 1,000 cP, 2,000 cP, 3,000 cP, 4,000 cP, 5,000 cP, 10,000 cP, 15,000 cP, 20,000 cP, 25,000 cP, 30,000 cP, 35,000 cP, 40,000 cP, 45,000 cP, 50,000 cP, 55,000 cP, 60,000 cP, 65,000 cP, 70,000 cP, 75,000 cP, 80,000 cP, 85,000 cP, 90,000 cP, or 95,000 cP. In some embodiments, the viscosity of the composition can be in the range of about 100 to 20,000 cP, or 1,000 cP about 20,000 cP. In other embodiments, the viscosity of the composition can be in the range of about 12,000 cP to about 20,000 cP. These viscosity ranges can be approximate and can be modified to achieve specific characteristics desired and/or required in the composition.

The compositions described herein may further include an additive known in the art. In some embodiments, the additive includes a compound that improves the composition for the mode of administration. In some embodiments, the additive improves the efficacy of the composition. In some embodiments, the additive improves the shelf life of the composition. In some embodiments, the additive is included for aesthetic purposes to improve the appearance, texture, scent, or feel of the composition. Exemplary additives for including in the compositions described herein include moisturizers, humectants, pigments, dyes, pearlescent compounds, nacreous pigments, bismuth oxychloride coated mica, titanium dioxide coated mica, colorants, fragrances, biocides, preservatives, lipolytic agent, diuretics, xanthines (such as caffeine, theophylline, and aminophylline), alpha hydroxy acids, antioxidants, lymphatic drainage agent, antiperspirant agents, exfoliants, hormones, enzymes, medicinal compounds, vitamins, minerals, electrolytes, alcohols, polyols, polypropylene glycol, retinoids, retinol, polyisobutene, polyoxyethylene, behenic acid, behenyl, sugar-alcohols, absorbing agents for ultraviolet radiation, botanical extracts, surfactants, silicone oils, organic oils, waxes, alkaline or acidic or buffering agents, film formers, thickening agents, hyaluronic acid, fumed silica, hydrated silica, talc, kaolin, starch, modified starch, mica, nylon, clay, bentonite, organo-modified clays, and combinations thereof.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion.

In some embodiments, the composition is formulated as a gel, sol, sol-gel, hydrogel, cream, foam, balm, liniment, unguent, colloid, emulsion, dispersion, salve, emollient, lotion, meltable solid, mousse, ointment, paste, serum, solution, spray, stick, liquid, or suspension.

II. Method of Making the Composition

Some embodiments provided herein relate to a method of making the composition described herein. Methods of making the composition include providing a saline solution. In some embodiments, the saline solution includes a reactive oxygen species, which may either be directly added to the saline solution or may be generated in the saline solution, for example, by electrolysis of the saline solution. The method further includes adding an emollient to the saline solution. In some embodiments, the method further includes adding a rheology agent to the saline solution to generate a composition of a desired viscosity. The desired viscosity will depend upon the final composition and method of application of the composition. For example, the desired viscosity may be a low viscosity composition, or the desired viscosity may be a high viscosity composition.

The saline solution may include electrolyzing a saline solution having a salt concentration of about 10 g NaCl/gal, such as 10.75 g NaCl/gal using a set of electrodes with an amperage of about 50-60 amps, such as 56 amps to produce an electrolyzed saline solution, wherein the water is chilled below room temperature and the water is circulated during electrolyzing. In some embodiments, the electrolysis is performed sufficient to generate a sufficient amount or concentration of hypochlorite. In some embodiments, electrolysis is performed sufficient to generate an amount of hypochlorite ranging from 1 to 1000 ppm, such as about 1, 2, 3, 4, 5, 6, 7, 8, 9, 10, 15, 20, 25, 30, 35, 40, 45, 50, 55, 60, 65, 70, 75, 80, 85, 90, 95, 100, 120, 150, 175, 200, 300, 400, 500, 600, 700, 800, 900, or 1000 ppm or an amount within a range defined by any two of the aforementioned amounts.

A method of producing the disclosed composition can include one or more of the steps of (1) preparation of an ultra-pure homogeneous solution of sodium chloride in water, (2) temperature control and flow regulation through a set of inert catalytic electrodes, and (3) a modulated electrolytic process that results in the formation of such stable molecular moieties and complexes. In one embodiment, such a process includes all these steps. In some embodiments, the method further includes mixing a rheology agent with the electrolyzed saline solution to a desired viscosity.

The saline generally should be free from contaminants, both organic and inorganic, and homogeneous down to the molecular level. In particular, metal ions can interfere with the electro-catalytic surface reactions, and thus it may be helpful for metals to be avoided. In one embodiment, a brine solution is used to salinate the water. The brine solution can have a NaCl concentration of about 540 g NaCl/gal, such as 537.5 g NaCl/gal.

In one embodiment, the method of making a composition as described herein can include reverse osmosis. As used herein, the term "reverse osmosis" refers to a process of extracting water through a semi-permeable membrane from feed water by applying on the feed water a pressure that is higher than the osmotic pressure of the feed water. Water can be supplied from a variety of sources, including but not limited to municipal water, filtered water, distilled water, nanopure water, or the like.

The reverse osmosis process can vary, but can include providing water having a total dissolved solid content of less than about 10 ppm, such as about 9 ppm, about 8 ppm, about 7 ppm, about 6 ppm, about 5 ppm, about 4 ppm, about 3 ppm, about 2 ppm, about 1 ppm or less.

The reverse osmosis process can be performed at a temperature of about 5° C., about 10° C., about 15° C., about 20° C., about 25° C., about 30° C., about 35° C., or a temperature within a range defined by any two of the aforementioned values. The reverse osmosis step can be repeated as needed to achieve a particular total dissolved solids level. In some embodiments, a distillation step can also be performed, prior to, after, or concomitant with the reverse osmosis step. Distillation as used herein refers to a process boiling water and condensing steam into a separate container to obtain distilled water. Distilled water includes water that is purified to remove minerals such as calcium and magnesium, trace elements, or other impurities by distillation. In some embodiments, distilled water is purchased and used in one or more of the above processes.

Other means of reducing contaminants include filtration and/or purification such as by utilizing deionization, carbon filtration, double-distillation, electrodeionization, resin filtration such as with Milli-Q purification, microfiltration, ultrafiltration, ultraviolet oxidation, electrodialysis, or combinations thereof.

The distillation process can vary, but can provide water having a total dissolved solid content of less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or less, or an amount within a range defined by any two of the aforementioned values. The temperature of the distillation process can be performed at a temperature of about 5° C., about 10° C., about 15° C., about 20° C., about 25° C., about 30° C., about 35° C., or a temperature within a range defined by any two of the aforementioned values.

The distillation step can be repeated as needed to achieve a particular total dissolved solids level. After water has been subjected to reverse osmosis, distillation, both, or neither, the level of total dissolved solids in the water can be less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or less, or an amount within a range defined by any two of the aforementioned values.

The reverse osmosis, distillation, both, or neither, can be preceded by a carbon filtration step. Purified water can be used directly with the systems and methods described herein.

In one embodiment, contaminants can be removed from a commercial source of water by the following procedure: water flows through an activated carbon filter to remove the aromatic and volatile contaminants and then undergoes reverse osmosis (RO) filtration to remove dissolved solids and most organic and inorganic contaminants. The resulting filtered RO water can contain less than about 8 ppm of dissolved solids. Most of the remaining contaminants can be removed through a distillation process, resulting in dissolved solid measurements less than 1 ppm. In addition to removing contaminants, distillation may also serve to condition the water with the correct structure and oxidation reduction potential (ORP) to facilitate the oxidative and reductive reaction potentials on the platinum electrodes in the subsequent electro-catalytic process.

After water has been subjected to reverse osmosis, distillation, both or neither, a salt can be added to the water in a salting step. The salt can be unrefined, refined, caked, de-caked, or the like. In some embodiments, the salt is halite, table salt, refined salt, curing salt, flake salt, Epsom salt, sea salt, Alaea salt (or Hawaiian sea salt), Alpenbergkern salt, Anglesey Sea salt, Celtic sea salt, Dead Sea salt, Himalayan sea salt (including Himalayan pink sea salt), Kalahari salt, Maras salt, Murray River salt flakes, Namibian salt pearls, Persian blue fine salt, Polish mine salt, primordial sea salts, Sal de Tavira, Sale Marino di Trapani, Sel de Guérande, South African Sea salt, Utah salt, black lava salt, brine, rock salt, red rock salt, fleur de sel, or kosher salt. The salt present in the composition can include a number of elements, including actinium, aluminum, antimony, arsenic, astatine, barium, beryllium, bismuth, boron, bromine, cadmium, calcium, carbon, cerium, cesium, chlorine, chromium, cobalt, copper, dysprosium, erbium, europium, francium, fluorine, gadolinium, gallium, germanium, gold, hafnium, holmium, hydrogen, iodine, indium, iridium, iron, lanthanum, lead, lithium, lutetium, magnesium, manganese, mercury, molybdenum, neptunium, neodymium, nickel, niobium, nitrogen, osmium, oxygen, palladium, phosphorus, platinum, plutonium, polonium, potassium, praseodymium, promethium, protactinium, radium, rhenium, rhodium, rubidium, ruthenium, samarium, scandium, selenium, silicon, silver, sodium, strontium, sulfur, tantalum, technetium, tellurium, terbium, thallium, thorium, thulium, tin, titanium, uranium, vanadium, ytterbium, zinc, or zirconium. In some embodiments, the element present in the salt can be present in an amount of less than 0.001 ppm to an amount of greater than 400,000 ppm.

In some embodiments, the salt includes aluminum in an amount of 114.8 ppm, antimony in an amount of 0.022 ppm, arsenic in an amount of 0.066 ppm, barium in an amount of 0.664 ppm, beryllium in an amount of 0.051 ppm, bismuth in an amount of 0.005 ppm, bromine in an amount of 56.006 ppm, cadmium in an amount of 0.017 ppm, calcium in an amount of 2101.000 ppm, chromium in an amount of 0.207 ppm, cobalt in an amount of 0.033 ppm, copper in an amount of 0.116 ppm, germanium in an amount of 0.072 ppm, iodide in an amount of less than 0.001 ppm, iron in an amount of 81.722 ppm, lead in an amount of 0.093 ppm, magnesium in an amount of 1944.000 ppm, manganese in an amount of 1.911 ppm, mercury in an amount of 0.016 ppm, molybdenum in an amount of 0.011 ppm, nickel in an amount of 0.096 ppm, phosphorus in an amount of 5.125 ppm, potassium in an amount of 1728.000 ppm, selenium in an amount of 0.269 ppm, silver in an amount of 0.004 ppm, sodium in an amount of 388690.000 ppm, strontium in an amount of 32.223 ppm, tin in an amount of 0.169 ppm, or zinc in an amount of 1.261 ppm or any combination thereof. In some embodiments, the salt may include one or more of the above elements present in an amount 1, 2, 3, 4, 5, 6, 7, 8, 9, or 10% higher or lower than the above-listed amounts.

In some embodiments, the salt includes aluminum in an amount of 32.473 ppm, antimony in an amount of 0.013 ppm, arsenic in an amount of 0.046 ppm, barium in an amount of 0.343 ppm, beryllium in an amount of 0.030 ppm, bismuth in an amount of 0.004 ppm, bromine in an amount of 70.607 ppm, cadmium in an amount of 0.010 ppm, calcium in an amount of 1290.000 ppm, chromium in an amount of 0.195 ppm, cobalt in an amount of 0.013 ppm, copper in an amount of 0.090 ppm, germanium in an amount of 0.085 ppm, iodide in an amount of less than 0.001 ppm, iron in an amount of 23.292 ppm, lead in an amount of 0.077 ppm, magnesium in an amount of 1304.000 ppm, manganese in an amount of 1.040 ppm, mercury in an amount of 0.009 ppm, molybdenum in an amount of 0.014 ppm, nickel in an amount of 0.086 ppm, phosphorus in an amount of 3.548 ppm, potassium in an amount of 1174.000 ppm, selenium in an amount of 0.235 ppm, silver in an amount of 0.002 ppm, sodium in an amount of 391706.000 ppm, strontium in an amount of 18.328 ppm, tin in an amount of 0.135 ppm, or zinc in an amount of 1.045 ppm or any combination thereof. In some embodiments, the salt may include one or more of the above elements present in an amount 1, 2, 3, 4, 5, 6, 7, 8, 9, or 10% higher or lower than the above-listed amounts.

In some embodiments, the salt includes aluminum in an amount of 241.700 ppm, antimony in an amount of 0.026 ppm, arsenic in an amount of 0.076 ppm, barium in an amount of 7.615 ppm, beryllium in an amount of 0.070 ppm, bismuth in an amount of 0.006 ppm, bromine in an amount of 7.789 ppm, cadmium in an amount of 0.024 ppm, calcium in an amount of 1860.000 ppm, chromium in an amount of 0.175 ppm, cobalt in an amount of 0.058 ppm, copper in an amount of 0.279 ppm, germanium in an amount of 0.092 ppm, iodide in an amount of less than 0.001 ppm, iron in an amount of 141.400 ppm, lead in an amount of 0.210 ppm, magnesium in an amount of 217.900 ppm, manganese in an amount of 11.804 ppm, mercury in an amount of 0.012 ppm, molybdenum in an amount of 0.037 ppm, nickel in an amount of 0.113 ppm, phosphorus in an amount of 39.541 ppm, potassium in an amount of 149.300 ppm, selenium in an amount of 0.226 ppm, silver in an amount of 0.006 ppm, sodium in an amount of 390600.000 ppm, strontium in an amount of 11.251 ppm, tin in an amount of 0.177 ppm, or zinc in an amount of 1.883 ppm or any combination thereof.

In some embodiments, the salt may include one or more of the above elements present in an amount 1, 2, 3, 4, 5, 6, 7, 8, 9, or 10% higher or lower than the above-listed amounts.

In some embodiments, the salt includes aluminum in an amount of 0.747 ppm, antimony in an amount of 0.014 ppm, arsenic in an amount of 0.039 ppm, barium in an amount of 0.012 ppm, beryllium in an amount of 0.038 ppm, bismuth in an amount of 0.005 ppm, bromine in an amount of 81.414 ppm, cadmium in an amount of 0.007 ppm, calcium in an amount of 10.625 ppm, chromium in an amount of 0.027 ppm, cobalt in an amount of 0.001 ppm, copper in an amount of 0.053 ppm, germanium in an amount of 0.081 ppm, iodide in an amount of less than 0.001 ppm, iron in an amount of 0.639 ppm, lead in an amount of 25.908 ppm, magnesium in an amount of 3.753 ppm, manganese in an amount of 0.040 ppm, mercury in an amount of 0.013 ppm, molybdenum in an amount of 0.007 ppm, nickel in an amount of 0.016 ppm, phosphorus in an amount of 3.690 ppm, potassium in an amount of 60.756 ppm, selenium in an amount of 0.202 ppm, silver in an amount of 0.002 ppm, sodium in an amount of 391290.000 ppm, strontium in an amount of 0.230 ppm, tin in an amount of 0.166 ppm, or zinc in an amount of 0.791 ppm or any combination thereof. In some embodiments, the salt may include one or more of the above elements present in an amount 1, 2, 3, 4, 5, 6, 7, 8, 9, or 10% higher or lower than the above-listed amounts.

In some embodiments, the salt is included in an amount of 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5, 6, 7, 8, 9, 10, 11, 12, 13, 14, or 15% (w/v), or an amount within a ranged defined by any two of the aforementioned values.

In one embodiment, the salt is sodium chloride (NaCl), lithium chloride (LiCl), hydrogen chloride (HCl), copper chloride ($CuCl_2$), copper sulfate ($CuSO_4$), potassium chloride (KCl), magnesium chloride (MgCl), calcium chloride ($CaCl_2$), or sulfates or phosphates. In some embodiments, the salt can include an additive. Salt additives can include, but are not limited to potassium iodide, sodium iodide, sodium iodate, dextrose, sodium fluoride, sodium ferrocyanide, tricalcium phosphate, calcium carbonate, magnesium carbonate, fatty acids, magnesium oxide, silicon dioxide, calcium silicate, sodium aluminosilicate, calcium aluminosilicate, ferrous fumarate, iron, or folic acid. Any of these additives can be added at this point or at any point during the described process. For example, the above additives can be added just prior to packaging the composition.

In another embodiment, the process can be applied to any ionic, soluble salt mixture, especially with those containing chlorides. In addition to NaCl, other non-limiting examples include LiCl, HCl, $CuCl_2$, $CuSO_4$, KCl, MgCl, $CaCl_2$, sulfates and phosphates. For example, strong acids such as sulfuric acid ($H_2SO_4$), and strong bases such as potassium hydroxide (KOH), and sodium hydroxide (NaOH) are frequently used as electrolytes due to their strong conducting abilities. Preferably the salt is sodium chloride (NaCl). A brine solution can be used to introduce the salt into the water. The amount of brine or salt may be apparent to one of ordinary skill in the art.

Salt can be added to water in the form of a brine solution. To mix the brine solution, a physical mixing apparatus can be used or a circulation or recirculation can be used. In one embodiment, pure pharmaceutical grade sodium chloride is dissolved in the prepared distilled water to form a 15 wt. % sub-saturated brine solution and continuously re-circulated and filtered until the salt has completely dissolved and all particles >0.1 microns are removed. This step can take several days. In one embodiment, the filtered, dissolved brine solution can be injected into tanks of distilled water in about a 1:352 ratio (salt:water) to form a 0.3% saline solution. In one embodiment, a ratio 10.75 g of salt per 1 gallon of water can be used to form the composition. In another embodiment, 10.75 g of salt in about 3-4 g of water, such as 3,787.5 g of water can be used to form the composition. This solution then can be allowed to re-circulate and diffuse until homogeneity at the molecular scale has been achieved.

In one embodiment, the homogenous saline solution is chilled to about 4.8±0.5° C. Temperature regulation during the entire electro-catalytic process is typically required as thermal energy generated from the electrolysis process itself may cause heating. In one embodiment, process temperatures at the electrodes can be constantly cooled and maintained at about 4.8° C. throughout electrolysis.

Brine can then be added to the previously treated water or to fresh untreated water to achieve a NaCl concentration of between about 1 g NaCl/gal water and about 25 g NaCl/gal water, between about 8 g NaCl/gal water and about 12 g NaCl/gal water, or between about 4 g NaCl/gal water and about 16 g NaCl/gal water. Once brine is added to water at an appropriate amount, the solution can be thoroughly mixed. The temperature of the liquid during mixing can be at room temperature or controlled to a desired temperature or temperature range.

To mix the solution, a physical mixing apparatus can be used or circulation or recirculation can be used. The salt solution can be chilled in a chilling step.

For large amounts of electrolyzed solution, various chilling and cooling methods can be employed. For example cryogenic cooling using liquid nitrogen cooling lines can be used. Likewise, the solution can be run through propylene glycol heat exchangers to achieve the desired temperature. The chilling time can vary depending on the amount of liquid, the starting temperature and the desired chilled temperature.

Products from the anodic reactions can be effectively transported to the cathode to provide the reactants to form the stable complexes on the cathode surfaces. Maintaining a high degree of homogeneity in the fluids circulated between the catalytic surfaces can also be helpful. A constant flow of about 2-8 mL/cm$^2$ per sec can be used, with typical mesh electrode distances 2 cm apart in large tanks. This flow can be maintained, in part, by the convective flow of gasses released from the electrodes during electrolysis.

The mixed solution, chilled or not, can then undergo electrochemical processing through the use of at least one electrode in an electrolyzing step. Each electrode can be or include a conductive metal. Metals can include, but are not limited to copper, aluminum, titanium, rhodium, platinum, silver, gold, iron, a combination thereof or an alloy such as steel or brass. The electrode can be coated or plated with a different metal such as, but not limited to aluminum, gold, platinum or silver. In one embodiment, each electrode is formed of titanium and plated with platinum. The platinum surfaces on the electrodes by themselves can be optimal to catalyze the required reactions. Rough, double layered platinum plating can assure that local "reaction centers" (sharply pointed extrusions) are active and that the reactants not make contact with the underlying electrode titanium substrate.

In one embodiment, rough platinum-plated mesh electrodes in a vertical, coaxial, cylindrical geometry can be optimal, with, for example, not more than 2.5 cm, not more than 5 cm, not more than 10 cm, not more than 20 cm, or not more than 50 cm separation between the anode and cathode. The amperage run through each electrode can be between about 2 amps and about 15 amps, between about 4 amps and about 14 amps, at least about 2 amps, at least about 4 amps, at least about 6 amps, or any range created using any of these values. In one embodiment, 7 amps is used with each electrode.

The amperage can be running through the electrodes for a sufficient time to electrolyze the saline solution. The solution can be chilled during the electrochemical process. The solution can also be mixed during the electrochemical process. This mixing can be performed to ensure substantially complete electrolysis.

Electric fields between the electrodes can cause movement of ions. Negative ions can move toward the anode and positive ions toward the cathode. This can enable exchange of reactants and products between the electrodes. In some embodiments, no barriers are needed between the electrodes.

After amperage has been run through the solution for a sufficient time, an electrolyzed solution is created. The solution can be stored and or tested for particular properties in storage/testing step.

The end products of this electrolytic process can react within the saline solution to produce many different reactive oxygen species. ROS can include, but are not limited to superoxides ($O_2^{*-}$, $HO_2^*$), hypochlorites ($OCl^-$, $HOCl$, $NaClO$), hypochlorates ($HClO_2$, $ClO_2$, $HClO_3$, $HClO_4$), oxygen derivatives ($O_2$, $O_3$, $O_4^{*-}$, O), hydrogen derivatives ($H_2$, $H^-$), hydrogen peroxide ($H_2O_2$), hydroxyl free radical ($OH^{*-}$), ionic compounds ($Na^+$, $Cl^-$, $H^+$, $OH^-$, $NaCl$, $HCl$, $NaOH$), chlorine ($Cl_2$), water clusters ($n*H_2O$—induced dipolar layers around ions), and combinations thereof. Some ROS can be electron acceptors and some can be electron donors. In some embodiments, a reactive oxygen species is a hypochlorite. Some reactive oxygen species are electron acceptors and include $HOCl$, $NaClO$, $O_2$, $H_2$, $H^+$, $ClO$, $Cl_2$, $H_2O_2$ and some are electron donors and include $O_2^-$, $HO_2$, $Cl^-$, $H^-$, $*OCl$, $O_3$, $*O_2^-$ and $OH^-$.

The chlorine concentration of the electrolyzed solution can be between about 5 ppm and about 34 ppm, between about 10 ppm and about 34 ppm, or between about 15 ppm and about 34 ppm. In one embodiment, the chlorine concentration is about 32 ppm.

The composition generally can include electrolytic and/or catalytic products of pure saline that mimic redox signaling molecular compositions of native salt water compounds found in and around human cells. The composition can be fine-tuned to mimic or mirror molecular compositions of different biological media. The composition can have reactive species other than chlorine present. As described, species present in the compositions described herein can include, but are not limited to $O_2$, $H_2$, $Cl_2$, $OCl^-$, $HOCl$, $NaOCl$, $HClO_2$, $ClO_2$, $HClO_3$, $HClO_4$, $H_2O_2$, $Na^+$, $Cl^-$, $H^+$, $H^-$, $OH^-$, $O_3$, $O_4^{*-}$, $^1O_2$, $OH^{*-}$, $HOCl$—$O_2^{*-}$, $HOCl$—$O_3$, $O_2^{*-}$, $HO_2^*$, $NaCl$, $HCl$, $NaOH$, and water clusters: $n*H_2O$-induced dipolar layers around ions, and the like.

In some embodiments, the saline solution is electrolyzed to produce an amount of active species, which may include including ozone, active chlorine, active oxygen, or active hydrogen species. In some embodiments, the ozone is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, 100, 150, 200, 250, or 300 ppm or an amount within a range defined by any two of the aforementioned values. In some embodiments, the active chorine species is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50,60, 70, 80, 90, 100, 150, 200, 250, or 300 ppm or an amount within a range defined by any two of the aforementioned values. In some embodiments, the active chorine species is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50,60, 70, 80, 90, 100, 150, 200, 250, or 300 ppm or an amount within a range defined by any two of the aforementioned values. In some embodiments, the active oxygen species is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50,60, 70, 80, 90, 100, 150, 200, 250, or 300 ppm or an amount within a range defined by any two of the aforementioned values. In some embodiments, the active hydrogen species is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50,60, 70, 80, 90, 100, 150, 200, 250, or 300 ppm or an amount within a range defined by any two of the aforementioned values. The process of electrolysis may be performed using any suitable voltage, current, time, or conditions to prepare the saline solution according to the desired concentration of active species.

Pulsing potentials in the power supply of the production units can be built into a system for making the composition. Lack of filter capacitors in the rectified power supply can cause the voltages to drop to zero 120 times per second, resulting in a hard spike when the alternating current in the house power lines changes polarity. This hard spike, under Fourier transform, can emit a large bandwidth of frequencies. In essence, the voltage is varying from high potential to zero 120 times a second. In other embodiments, the voltage can vary from high potential to zero about 1,000 times a second, about 500 times a second, about 200 times a second, about 150 times a second, about 120 times a second, about 100 times a second, about 80 times a second, about 50 times a second, about 40 times a second, about 20 times a second, between about 200 times a second and about 20 times a second, between about 150 times a second and about 100 times a second, at least about 100 times a second, at least about 50 times a second, or at least about 120 times a second. This power modulation can allow the electrodes sample all voltages and also provides enough frequency bandwidth to excite resonances in the forming molecules themselves. The time at very low voltages can also provide an environment of low electric fields where ions of similar charge can come within close proximity to the electrodes. All of these factors together can provide a possibility for the formation of stable complexes capable of generating and preserving ROS free radicals.

Waveforms with an alternating current (AC) ripple can be used to provide power to the electrodes. Such an AC ripple can also be referred to as pulse or spiking waveforms and include: any positive pulsing currents such as pulsed waves, pulse train, square wave, saw tooth wave, pulse-width modulation (PWM), pulse duration modulation (PDM), single phase half wave rectified AC, single phase full wave rectified AC or three phase full wave rectified for example.

A bridge rectifier may be used. Other types of rectifiers can be used such as Single-phase rectifiers, Full-wave rectifiers, Three-phase rectifiers, Twelve-pulse bridge, Voltage-multiplying rectifiers, filter rectifier, a silicon rectifier, an SCR type rectifier, a high-frequency (RF) rectifier, an inverter digital-controller rectifier, vacuum tube diodes, mercury-arc valves, solid-state diodes, silicon-controlled rectifiers and the like. Pulsed waveforms can be made with a transistor regulated power supply, a dropper type power supply, a switching power supply and the like.

This pulsing waveform model can be used to stabilize superoxides, hydroxyl radicals and OOH* from many different components and is not limited to any particular variable such as voltage, amps, frequency, flux (current density) or current. The variables are specific to the components used. For example, water and NaCl can be combined which provide molecules and ions in solution. A 60 Hz current can be used, meaning that there are 60 cycles/120 spikes in the voltage (V) per second or 120 times wherein the V is 0 each second. When the V goes down to 0 it is believe that the 0 V allows for ions to drift apart/migrate and reorganize before the next increase in V. Without wishing to be bound by theory, the spiking in V allows for and promotes a variable range of frequencies influencing many different types of compounds and/or ions.

Diodes may also be used. The V may drop to 0 as many times per second as the frequency is adjusted. As the frequency is increased the number of times the V drops is increased.

When the ions are affected by the electricity from the electrodes, they change. While still not wishing to be bound by theory, it is believed that the electricity alters the state of some of the ions/compounds. This alteration results in the pushing of electrons out of their original orbit and/or spin state into a higher energy state and/or a single spin state. This electrolysis provides the energy to form free radicals which are ultimately formed during a multi-generational cycling of reactants and products during the electrolysis process. In other words, compounds and/or ions are initially electrolyzed so that the products that are formed are then themselves reacted with other compounds and/or ions and/or gas to form a second generation of reactants and products. This generational process then happens again so that the products from the second generation react with other compounds and/or ions in solution when the voltage spikes again.

In some embodiments, the redox potential can be about 840 mV. In some embodiments, the frequency can be from about 1 Hz to infinity or to about 100 MHz.

In some embodiments, end products of the electrolytic process can react within the saline solution to produce different chemical entities. The compositions described herein can include one or more of these chemical entities. These end products can include, but are not limited to superoxides: $O_2^{*-}$, $HO_2^*$; hypochlorites: $OCl^-$, $HOCl$, $NaOCl$; hypochlorates: $HClO_2$, $ClO_2$, $HClO_3$, $HClO_4$; oxygen derivatives: $O_2$, $O_3$, $O_4^{*-}$, $^1O$; hydrogen derivatives: $H_2$, $H^-$; hydrogen peroxide: $H_2O_2$; hydroxyl free Radical: $OH^{*-}$; ionic compounds: $Na^+$, $Cl^-$, $H^+$, $OH^-$, $NaCl$, $HCl$, $NaOH$; chlorine: $Cl_2$; and water clusters: $n*H_2O$-induced dipolar layers around ions, several variations.

To determine the relative concentrations and rates of production of each of these during electrolysis, certain general chemical principles can be helpful:

1) A certain amount of Gibbs free energy is required for construction of the molecules; Gibbs free energy is proportional to the differences in electrode potentials. Reactions with large energy requirements are less likely to happen, for example an electrode potential of −2.71 V (compared to hydrogen reduction at 0.00 V) is required to make sodium metal: $Na^+ + e^- \rightarrow Na(s)$.

Such a large energy difference requirement makes this reaction less likely to happen compared to other reactions with smaller energy requirements. Electron(s) from the electrodes may be preferentially used in the reactions that require lesser amounts of energy, such as the production of hydrogen gas.

2) Electrons and reactants are required to be at the same micro-locality on the electrodes. Reactions that require several reactants may be less likely to happen, for example: $Cl_2 + 6 H_2O \rightarrow 10e^- + 2 ClO_3^- + 12 H^+$.

This reaction requires six water molecules and one $Cl_2$ molecule to be at the electrode at the same point at the same time and a release of 10 electrons to simultaneously occur. The probability of this happening generally is smaller than other reactions requiring fewer and more concentrated reactants to coincide, but such a reaction may still occur.

3) Reactants generated in preceding generations can be transported or diffuse to the electrode where reactions happen. For example, dissolved oxygen ($O_2$) produced on the anode from the first generation can be transported to the cathode in order to produce superoxides and hydrogen peroxide in the second generation. Ions can be more readily transported: they can be pulled along by the electric field due to their electric charge. In order for chlorates, to be generated, for example, $HClO_2$ can first be produced to start the cascade, restrictions for $HClO_2$ production can also restrict any subsequent chlorate production. Lower temperatures can prevent $HClO_2$ production.

Stability and concentration of the above products can depend, in some cases substantially, on the surrounding environment. The formation of complexes and water clusters can affect the lifetime of the moieties, especially the free radicals.

In a pH-neutral aqueous solution (pH around 7.0) at room temperature, superoxide free radicals ($O_2^{*-}$) have a half-life of 10's of milliseconds and dissolved ozone ($O_3$) has a half-life of about 20 minutes. Hydrogen peroxide ($H_2O_2$) is relatively long-lived in neutral aqueous environments, but this can depend on redox potentials and UV light. Other entities such as HCl and NaOH rely on acidic or basic environments, respectively, in order to survive. In pH-neutral solutions, $H^+$ and $OH^-$ ions have concentrations of approximately 1 part in 10,000,000 in the bulk aqueous solution away from the electrodes. $H^-$ and $^1O$ can react quickly. The stability of most of these moieties mentioned above can depend on their microenvironment.

Superoxides and ozone can form stable van der Waals molecular complexes with hypochlorites. Clustering of polarized water clusters around charged ions can also have the effect of preserving hypochlorite-superoxide and hypochlorite-ozone complexes. Such complexes can be built through electrolysis on the molecular level on catalytic substrates, and may not occur spontaneously by mixing together components. Hypochlorites can also be produced spontaneously by the reaction of dissolved chlorine gas ($Cl_2$) and water. As such, in a neutral saline solution the formation of one or more of the stable molecules and complexes may exist: dissolved gases: $O_2$, $H_2$, $Cl_2$; hypochlorites: $OCl^-$, HOCl, NaOCl; hypochlorates: $HClO_2$, $ClO_2$, $HClO_3$, $HClO_4$; hydrogen peroxide: $H_2O_2$; ions: $Na^+$, $Cl^-$, $H^+$, $H^-$, $OH^-$; ozone: $O_3$, $O_4^{*-}$; singlet oxygen: $^1O$; hydroxyl free radical: $OH^{*-}$; superoxide complexes: $HOCl—O_2^{*-}$; and ozone complexes: $HOCl—O_3$. One or more of the above molecules can be found within the compositions described herein.

A complete quantum chemical theory can be helpful because production is complicated by the fact that different temperatures, electrode geometries, flows and ion transport mechanisms and electrical current modulations can materially change the relative/absolute concentrations of these components, which could result in producing different distinct compositions. As such, the selection of production parameters can be critical. The amount of time it would take to check all the variations experimentally may be prohibitive.

The chlorine concentration of the electrolyzed solution can be about 5 ppm, about 10 ppm, about 15 ppm, about 20 ppm, about 21 ppm, about 22 ppm, about 23 ppm, about 24 ppm, about 25 ppm, about 26 ppm, about 27 ppm, about 28 ppm, about 29 ppm, about 30 ppm, about 31 ppm, about 32 ppm, about 33 ppm, about 34 ppm, about 35 ppm, about 36 ppm, about 37 ppm, about 38 ppm, less than about 38 ppm, less than about 35 ppm, less than about 32 ppm, less than about 28 ppm, less than about 24 ppm, less than about 20 ppm, less than about 16 ppm, less than about 12 ppm, less than about 5 ppm, between about 30 ppm and about 34 ppm, between about 28 ppm and about 36 ppm, between about 26 ppm and about 38 ppm, between about 20 ppm and about 38 ppm, between about 5 ppm and about 34 ppm, between about 10 ppm and about 34 ppm, or between about 15 ppm and about 34 ppm. In one embodiment, the chlorine concentration is about 32 ppm. In another embodiment, the chlorine concentration is less than about 41 ppm.

The saline concentration in the electrolyzed solution can be about 0.10% w/v, about 0.11% w/v, about 0.12% w/v, about 0.13% w/v, about 0.14% w/v, about 0.15% w/v, about 0.16% w/v, about 0.17% w/v, about 0.18% w/v, about 0.19% w/v, about 0.20% w/v, about 0.30% w/v, about 0.40% w/v, about 0.50% w/v, about 0.60% w/v, about 0.70% w/v, between about 0.10% w/v and about 0.20% w/v, between about 0.11% w/v and about 0.19% w/v, between about 0.12% w/v and about 0.18% w/v, between about 0.13% w/v and about 0.17% w/v, or between about 0.14% w/v and about 0.16% w/v.

The composition generally can include electrolytic and/or catalytic products of pure saline that mimic redox signaling molecular compositions of the native salt water compounds found in and around human cells. The composition can be fine-tuned to mimic or mirror molecular compositions of different biological media. The composition can have reactive species other than chlorine present. As described, species present in the compositions described herein can include, but are not limited to $O_2$, $H_2$, $Cl_2$, $OCl^-$, HOCl, NaOCl, $HClO_2$, $ClO_2$, $HClO_3$, $HClO_4$, $H_2O_2$, $Na^+$, $Cl^-$, $H^+$, $H^-$, $OH^-$, $O_3$, $O_4^{*-}$, $^1O$, $OH^{*-}$, $HOCl—O_2^{*-}$, $HOCl—O_3$, $O_2^*$, $HO_2^*$, NaCl, HCl, NaOH, and water clusters: $n*H_2O$—induced dipolar layers around ions, several variations.

In some embodiments, hydroxyl radicals can be stabilized in the composition by the formation of radical complexes. The radical complexes can be held together by hydrogen bonding. Another radical that can be present in the composition is an OOH* radical. Still other radical complexes can include a nitroxyl-peroxide radical (HNO—HOO*) and/or a hypochlorite-peroxide radical (HOCl—HOO*).

Concentrations of reactive species in the electrolyzed saline solutions, detected by fluorescence photo spectroscopy, may not significantly decrease in time. Mathematical models show that bound $HOCl—*O_2^-$ complexes are possible at room temperature. Molecular complexes can preserve volatile components of reactive species. For example, reactive species concentrations in whole blood as a result of molecular complexes may prevent reactive species degradation over time.

The electrolyzed saline solution having reactive oxygen species may further be mixed with a rheology agent.

III. Methods of Use of a Composition

The composition provided herein may be prepared, packaged, or sold in formulations for oral, injectable, or topical administration. The composition can be filled into suitable packaging (containers) such as, for example, syringes, tubes, cartons, capsule, jars, bottles, canisters, squeeze pack, pouches, packages, packets, sacks, tank, or other containers. In some embodiments, the composition may be ingested, injected, or may be applied directly to skin. In some embodiments, the composition may be applied by an applicator, a brush, or other device for application to the skin.

For oral application, the composition may be formulated as a liquid, a gel, or other composition suitable for ingestion. Similarly, for injection, the composition may be formulated as a solution or liquid injectable suitable for parenteral administration (for example, subcutaneous, intravenous, intramuscular, intramedullary, intrathecal, or other composition for parenteral administration). In some embodiments, the composition is administered orally or parenterally in ounce units such as from 0.1 oz. to 20 oz. or as desired by the subject. Each administration can be about 0.1 oz., 0.2 oz., 0.3 oz., 0.4 oz., 0.5 oz., 0.6 oz., 0.7 oz., 0.8 oz., 0.9 oz., 1 oz., about 2 oz., about 3 oz., about 4 oz., about 5 oz., about 6 oz., about 7 oz., about 8 oz., about 9 oz., about 10 oz., about 11 oz., about 12 oz., about 16 oz., or about 20 oz. The composition can be administered once, twice, three times, four times or more a day. In one embodiment, the composition administered at a rate of about 4 oz. twice a day. In some embodiments, the composition formulated for oral administration is provided or administered to a subject as a beverage. In some embodiments, the oral formulation exhibits superior taste. In some embodiments, the beverage improves endurance, improves metabolic activity, increases energy, increases health and well-being, improves hydration, treats or ameliorates a disease or disorder, or combats metabolic syndrome.

In some embodiments, the composition is formulated for topical application, for example to be applied directly to skin, such as a region of skin that would that would benefit from application. In other embodiments, the composition is applied directly to the skin by one or more of a dropper, an applicator stick, as a mist or aerosol, as a transdermal patch, by wiping with a wipe, or by spreading the composition on the area with fingers or other applicators. The composition can be applied to the skin in any suitable therapeutic amount. In some embodiments, the composition is administered and/or applied to the skin in ounce units such as from 0.1 oz. to 20 oz. or as desired by the subject. Each application to the skin can be about 0.1 oz., 0.2 oz., 0.3 oz., 0.4 oz., 0.5 oz., 0.6 oz., 0.7 oz., 0.8 oz., 0.9 oz., 1 oz., about 2 oz., about 3 oz., about 4 oz., about 5 oz., about 6 oz., about 7 oz., about 8 oz., about 9 oz., about 10 oz., about 11 oz., about 12 oz., about 16 oz., or about 20 oz. When applied to the skin, it can be applied once, twice, three times, four times or more a day. In one embodiment, the composition is applied to the skin at a rate of about 4 oz. twice a day. In some embodiments, the composition formulated for topical administration is provided or administered to a subject. In some embodiments, the topical formulation exhibits superior smoothness or lubricity. In some embodiments, the topical formulation improves the appearance of skin, reduces wrinkles or spots, increases skin elasticity, improves health and wellness, or treats or ameliorates a disease or disorder.

Packaging can include single use aliquots in single use packaging such as pouches. The composition can be packaged in suitable packaging having volumes of about 0.1 oz., about 0.2 oz., about 0.5 oz., about 1 oz., about 2 oz., about 4 oz., about 8 oz., about 16 oz., about 32 oz., about 48 oz., about 64 oz., about 80 oz., about 96 oz., about 112 oz., about 128 oz., about 144 oz., about 160 oz., or an amount within a range defined by any two of the aforementioned values. The packaging can also be squeezable pouches having similar volumes.

In some embodiments, packaging may be free of dyes, metal specks, or chemicals that can be dissolved by acids or oxidizing agents. In other embodiments, any bottles, package caps, bottling filters, valves, lines, and heads used in packaging may be specifically rated for acids and oxidizing agents. In some cases, package caps with any organic glues, seals, or other components sensitive to oxidation may be avoided since they could neutralize and weaken the product over time.

As used herein, a "subject" or a "patient" refers to an animal that is the object of treatment, administration, observation, or experiment. "Animal" comprises cold-and warm-blooded vertebrates and invertebrates such as fish, shellfish, reptiles and, in particular, mammals. "Mammal" comprises, without limitation, mice, rats, rabbits, guinea pigs, dogs, cats, sheep, goats, cows, horses, primates, such as monkeys, chimpanzees, and apes, and, in particular, humans. In some alternatives, the subject is human.

Some embodiments disclosed herein relate to selecting a subject or patient in need. In some embodiments, a patient is selected who is in need of treatment, amelioration, inhibition, progression, prophylaxis, or improvement in disease symptoms or who is in need of curative therapy. In some embodiments, a patient is selected who would benefit from application of a composition having reactive oxygen species therein. Such identification or selection of said subjects or patients in need can be made through clinical and/or diagnostic evaluation. In some embodiments, a subject is selected who does not have a disease condition, but who wishes to prevent a disease condition.

The term "therapeutically effective amount" is used to indicate an amount of a composition that elicits the biological or medicinal response indicated. For example, a therapeutically effective amount of a composition can be the amount needed to prevent, alleviate, or ameliorate a disease or condition or an appearance of a disease or condition. Determination of a therapeutically effective amount is within the capability of those skilled in the art, in view of the disclosure provided herein. The therapeutically effective amount of the composition disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, a dose is provided in an amount of about 0.1 ounce to about 12 ounces, such as 0.1, 0.2, 0.3, 0.4, 0.5, 0.6, 0.7, 0.8, 0.9, 1, 2, 3, 4, 5, 6, 7, 8, 9, 10, 11, or 12 ounces, or an amount within a range defined by any two of the aforementioned values. In some embodiments, the dose is administered at a frequency of four times daily to one time monthly, such as 4 times/day, 3 times/day, 2 times/day, 1 time/day, once every other day, 6 times/week, 5 times/week, 4 times/week, 3 times/week, 2 times/week, 1 time/week, once every other week, twice monthly, or once monthly, or an amount within a range defined by any two of the aforementioned frequencies. In some embodiments, the dose is administered for a period of one day to 10 years or more, for example, for a period of one day, one week, one month, six months, one year, two years, three years, four years, five years, six years, seven years, eight years, nine years, ten years, or more, or within a range defined by any two of the aforementioned values.

As used herein, the term "coadministration" of pharmacologically active compounds refers to the delivery of two or more separate chemical entities or separate therapies, whether in vitro or in vivo. Coadministration refers to the simultaneous delivery of separate agents or therapies; to the simultaneous delivery of a mixture of agents; to the delivery of one agent followed by delivery of a second agent or additional agents; or to the administration of one therapy followed by or concomitant with another therapy. In all cases, agents or therapies that are coadministered are intended to work in conjunction with each other. Similarly, in the context of administration of more than one compound, the term "in combination" refers to a concomitant delivery of one compound with one or more compounds. The compounds may be administered in combination by simultaneous administration or administration of one compound before or after administration of another compound.

In some embodiments, the composition may be administered or applied alone, in the absence of other treatments, therapies, or agents or in combination with one or more therapy for the treatment of a disease or condition.

In some embodiments, the composition may be applied directly into the skin, and therefore, the composition may be formulated for topical application. Accordingly, the composition may have any suitable form for topical administration. In some embodiments the composition is in the form of a cream, a hydrogel, a lotion, a gel, a serum, a liquid, a foam, a mist, or an ointment. In some embodiments, the composition may be formulated for intradermal or subcutaneous administration.

The disclosure is generally described herein using affirmative language to describe the numerous embodiments. The disclosure also includes embodiments in which subject matter is excluded, in full or in part, such as substances or materials, method steps and conditions, protocols, or procedures.

EXAMPLES

Some aspects of the embodiments discussed above are disclosed in further detail in the following examples, which are not in any way intended to limit the scope of the present disclosure. Those in the art will appreciate that many other embodiments also fall within the scope of the disclosure, as it is described herein above and in the claims.

Example 1

Preparation of Redox Compositions

The following example describes an embodiment of a composition and methods of making the composition.

A composition was prepared with the ingredients as provided in Table 1. The ingredients provided below were added to saline solution, with a final pH adjusted to 6.5–7.0. The saline solution was prepared with 0.05% salt.

TABLE 1

| Reactive Oxygen Composition | | |
|---|---|---|
| Ingredient | Final % wt/vol | Role in Composition |
| Electrolyzed Saline Solution (0.05% salt) | 94.628 | Base |
| Dimethicone Satin | 5 | Emollient |
| Sodium Hypochlorite (4.99%) | 0.072 | Reactive oxygen species |
| Sodium Phosphate Monobasic | 0.3 | pH modifier |

Refined salts, such as table salts can be used to prepare the saline solution, which may include the components listed in Table 2.

TABLE 2

| Refined table salt components used in saline solution | |
|---|---|
| Element | Quantity (ppm) |
| Aluminum | 0.747 |
| Antimony | 0.014 |
| Arsenic | 0.039 |
| Barium | 0.012 |
| Beryllium | 0.038 |
| Bismuth | 0.005 |
| Bromide | 81.414 |
| Cadmium | 0.007 |
| Calcium | 10.625 |
| Chromium | 0.027 |
| Cobalt | 0.001 |
| Copper | 0.053 |
| Germanium | 0.081 |
| Iodide | <0.001 |
| Iron | 0.639 |
| Lead | 25.908 |
| Magnesium | 3.753 |
| Manganese | 0.040 |
| Mercury | 0.013 |
| Molybdenum | 0.007 |
| Nickel | 0.016 |
| Phosphorus | 3.690 |
| Potassium | 60.756 |
| Selenium | 0.202 |
| Silver | 0.002 |
| Sodium | 391,290 |
| Strontium | 0.230 |
| Tin | 0.166 |
| Zinc | 0.791 |

The salt composition described in Table 2 is refined table salt, and the quantity of elements was determined by inductively couple plasma mass spectrometry (ICP-MS). Teachings in the art suggest that only purified, refined salts may be used in a saline solution having reactive oxygen species, such as hypochlorite, and that raw or unprocessed salts are incompatible for use in a saline solution having reactive oxygen species. Thus, not only can raw, unprocessed salts be used in the saline solution, but raw, unprocessed salts result in improved compositions that function unexpectedly superior to compositions prepared using traditional refined salts. The components for the improved salt composition using raw salt are provided in Table 3, in three separate salt compositions.

TABLE 3

| Raw salt components used in saline solution | | | |
|---|---|---|---|
| | Composition 1 | Composition 2 | Composition 3 |
| Element | | Quantity (ppm) | |
| Aluminum | 114.8 | 32.473 | 241.700 |
| Antimony | 0.022 | 0.013 | 0.026 |

TABLE 3-continued

Raw salt components used in saline solution

| Element | Composition 1 | Composition 2 Quantity (ppm) | Composition 3 |
|---|---|---|---|
| Arsenic | 0.066 | 0.046 | 0.076 |
| Barium | 0.664 | 0.343 | 7.615 |
| Beryllium | 0.051 | 0.030 | 0.070 |
| Bismuth | 0.005 | 0.004 | 0.006 |
| Bromide | 56.006 | 70.607 | 7.789 |
| Cadmium | 0.017 | 0.010 | 0.024 |
| Calcium | 2101.000 | 1290.000 | 1860.000 |
| Chromium | 0.207 | 0.195 | 0.175 |
| Cobalt | 0.033 | 0.013 | 0.058 |
| Copper | 0.116 | 0.090 | 0.279 |
| Germanium | 0.072 | 0.085 | 0.092 |
| Iodide | <0.001 | <0.001 | <0.001 |
| Iron | 81.722 | 23.292 | 141.400 |
| Lead | 0.093 | 0.077 | 0.210 |
| Magnesium | 1944.000 | 1304.000 | 217.900 |
| Manganese | 1.911 | 1.040 | 11.804 |
| Mercury | 0.016 | 0.009 | 0.012 |
| Moly bdenum | 0.011 | 0.014 | 0.037 |
| Nickel | 0.096 | 0.086 | 0.113 |
| Phosphorus | 5.125 | 3.548 | 9.541 |
| Potassium | 1728.000 | 1174.000 | 149.300 |
| Selenium | 0.269 | 0.235 | 0.226 |
| Silver | 0.004 | 0.002 | 0.006 |
| Sodium | 388690.000 | 391706.000 | 390600.000 |
| Strontium | 32.223 | 18.328 | 11.251 |
| Tin | 0.169 | 0.135 | 0.177 |
| Zinc | 1.261 | 1.045 | 1.883 |

The raw salt compositions provided in Table 3 were analyzed by ICP-MS to determine the quantity of elements. The salt compositions used were various types of raw sea salt (compositions 1 and 2—Himalayan pink sea salt; composition 3—sea salt).

The composition described in Table 1 exhibits unexpectedly superior results when the saline solution is prepared using a salt provided in Table 3, or other forms of raw salt described herein.

Example 2

Preparation of Gel Compositions

The following example describes an embodiment of a gel composition and methods of making the composition.

A gel composition was prepared using as described in Example 1 that further includes a rheology agent as provided in Table 4. The ingredients were added to the saline solution, with a final pH adjusted to 6.5-7.0. The saline solution was prepared with 0.05% salt, using the raw salt components described in Example 1.

TABLE 4

| Gel Composition | | |
|---|---|---|
| Ingredient | Final % wt/vol | Role in Composition |
| Electrolyzed Saline Solution (0.05% salt) | 91.378 | Base |
| Laponite XLG | 3.25 | Rheology agent |
| Dimethicone Satin | 5 | Emollient |
| Sodium Hypochlorite (4.99%) | 0.072 | Reactive oxygen species |
| Sodium Phosphate Monobasic | 0.3 | pH modifier |

Thus, not only can raw, unprocessed salts be used in the saline solution, but raw, unprocessed salts result in improved gel compositions that function unexpectedly superior to gel compositions prepared using traditional refined salts.

Example 3

Improved Oral Compositions

The following example describes methods of use of a composition as described herein formulated as a beverage for oral consumption.

An oral composition is formulated as described herein having an electrolyzed saline solution with a raw salt of Table 3. The composition is provided to subjects for oral consumption, who provide feedback on the formulation related to the taste of the formulation and to their general well-being and health following consumption of the formulation over a treatment period. Each subject is instructed to consume the formulation in an amount of 0.1 oz. to 20 oz., once, twice, three times, four times or more a day for the treatment period.

Control subjects are provided a control formulation having an electrolyzed saline solution with a refined salt as listed in Table 2, or are provided with beverages known in the art. The control subjects are instructed to provide feedback on the formulation related to the taste of the formulation and to their general well-being and health after consumption of the formulation over the treatment period.

The feedback from both the test and control subjects is collected and results are compared for the test and control formulation. The test formulation having the raw salts of Table 3 exhibits unexpectedly superior properties as compared to the control formulation having refined salts of Table 2. Furthermore, the test formulation exhibits improved properties as compared to existing beverages known in the art. Specifically, the test formulation having raw salts exhibits improved taste, provides greater endurance for the subject, provides greater energy for the subject, more effectively combats metabolic syndrome, provides better hydration, and increases the general health and well-being of the subject as compared to the control formulation and as compared to beverages known in the art. Thus, the oral formulation having raw unprocessed salts exhibits unexpectedly superior results as compared to the control formulation and as compared to beverages known in the art.

Example 4

Improved Topical Compositions

The following example describes methods of use of a composition as described herein formulated for topical application.

A topical composition is formulated as described in Table 4 having a raw salt described in Table 3. The composition is provided to subjects, who provide feedback on the formulation related to the feel and texture of the formulation and to improvements in physical appearance of skin after using the formulation over a treatment period. Each subject is instructed to apply the formulation in an amount of 0.1 oz. to 20 oz., once, twice, three times, four times or more a day for the treatment period.

The test formulation having the raw salts of Table 4 provides superior smoothness when provided topically to skin, assists in reducing wrinkles or spots, and improves the overall appearance of skin. Thus, the gel composition described in Table 4 exhibits unexpectedly superior results when the saline solution is prepared using a raw unprocessed salt.

The formulations described in Examples 1-4 having raw unprocessed salts (such as those described in Table 3) exhibits additional surprising characteristics. In particular, the method of manufacture of the electrolyzed saline solution is more efficient using raw unprocessed salts as compared to compositions prepared using refined salts. Furthermore, the compositions exhibit improved stability as compared to compositions prepared using refined salts. For example, the compositions remain stable for at least 3 months, at least 6 months, at least 9 months, at least 12 months, at least 15 months, at least 18 months, at least 21 months, at least 24 months, at least 30 months, at least 50 months, at least 100 months, or longer, and exhibit improved stability compared to compositions formulated using refined salts.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A composition, comprising:
   an electrolyzed saline solution, wherein the electrolyzed saline solution comprises Himalayan sea salt present in an amount of about 0.01% to about 15% w/v;
   a reactive oxygen species comprising hypochlorite, wherein the hypochlorite is present in an amount of about 60 to about 100 ppm;
   an emollient; and
   a pH modifier;
   the composition comprising an osmolality measurement value between about 0.5 and 100 mOsm/kg.

2. The composition of claim 1, wherein the osmolality measurement value is about 3 to 5 mOsm/kg.

3. The composition of claim 1, wherein the Himalayan sea salt is present in an amount of 0.05%, wherein the hypochlorite is present in an amount of 72 ppm, wherein the emollient is a silicone polymer present in an amount of 5% wt/vol, wherein the pH modifier is sodium phosphate monobasic present in an amount of 0.3% wt/vol, and further comprising sodium magnesium silicate present in an amount of 3.25% wt/vol.

4. The composition of claim 1, wherein the electrolyzed saline solution is present in an amount of 94.628% final wt/vol and comprises salt in an amount 0.05%, wherein the emollient comprises silicone polymer present in an amount of 5% final wt/vol, wherein the hypochlorite is present in an amount of 0.072% final wt/vol, and wherein the pH modifier is sodium phosphate monobasic present in an amount of 0.3% final wt/vol.

5. The composition of claim 1, wherein the electrolyzed saline solution is present in an amount of 91.378% final wt/vol and comprises salt in an amount of 0.05%, wherein the emollient comprises silicone polymer present in an amount of 5% final wt/vol, wherein the hypochlorite is present in an amount of 0.072% final wt/vol, wherein the pH modifier is sodium phosphate monobasic present in an amount of 0.3% final wt/vol, and further comprising sodium magnesium silicate present in an amount of 3.25% final wt/vol, wherein the composition is formulated as a gel.

6. The composition of claim 1 further comprising:
sodium magnesium silicate present in an amount of about 3% wt/vol; and
an additive selected from the group consisting of moisturizers, humectants, pigments, dyes, pearlescent compounds, nacreous pigments, bismuth oxychloride coated mica, titanium dioxide coated mica, colorants, fragrances, biocides, preservatives, lipolytic agents, diuretics, xanthines, alpha hydroxyl acids, antioxidants, lymphatic drainage agents, antiperspirant agents, exfoliants, hormones, enzymes, medicinal compounds, vitamins, minerals, electrolytes, alcohols, polyols, polypropylene glycol, retinoids, retinol, polyisobutene, polyoxyethylene, behenic acid, behenyl, sugar-alcohols, absorbing agents for ultraviolet radiation, botanical extracts, surfactants, silicone oils, organic oils, waxes, alkaline or acidic or buggering agents, film formers, thickening agents, hyaluronic acid, fumed silica, hydrated silica, talc, kaolin, starch, modified starch, mica, nylon, clay, bentonite, organo-modified clays, and combinations thereof,
wherein the composition is formulated as a topical formulation.

7. The composition of claim 1, wherein the composition has a pH ranging from about 6.0 to about 7.8.

8. The composition of claim 1, further comprising superoxides, hypochlorites, hypochlorates, oxygen derivatives, hydrogen derivatives, hydrogen peroxide, hydroxyl free radical, ionic compounds, chlorine, and water clusters.

9. The composition of claim 1, wherein the composition is formulated as a gel, sol, sol-gel, hydrogel, cream, foam, balm, liniment, unguent, colloid, emulsion, dispersion, salve, emollient, lotion, meltable solid, mousse, ointment, paste, serum, solution, liquid, spray, stick, or suspension.

10. The composition of claim 3, wherein the silicone polymer is amodimethicone, dimethicone, cyclomethicone, cyclodimethicone, iso-dimethicone copolymer, or a blend thereof.

11. The composition of claim 5, wherein the gel has a viscosity ranging from about 100 to about 100,000 centipoise (cP).

12. The composition of claim 6, wherein the exfoliant comprises lactic acid, glycolic acid, malic acid, tartaric acid, citric acid, salicylic acid, lactobionic acid, or gluconic acid.

13. The composition of claim 1, wherein the electrolyzed saline solution comprises ozone in an amount of about 0.1 to 300 ppm, active chlorine species in an amount of about 0.1 to 300 ppm, active oxygen species in an amount of about 0.1 to 300 ppm, and active hydrogen species in an amount of about 0.1 to 300 ppm.

14. The composition of claim 1, wherein the electrolyzed saline solution has a redox potential of 840 mV.

15. The composition of claim 1, wherein the composition is formulated in a dosage amount ranging from about 0.1 ounce to about 12 ounces.

16. The composition of claim 1, wherein the composition comprises:
Himalayan salt in an amount of about 0.05% w/v;
hypochlorite in an amount of about 72 ppm;
dimethicone in an amount of about 5% w/v; and
sodium phosphate monobasic in an amount of about 0.3% w/v,
wherein the composition has a pH ranging from about 6.5 to about 7.0.

17. The composition of claim 16, wherein the composition is a gel composition and further comprises sodium magnesium silicate in an amount of about 3.25% w/v.

* * * * *